United States Patent [19]

Dattagupta et al.

[11] Patent Number: 5,348,855
[45] Date of Patent: Sep. 20, 1994

[54] ASSAY FOR NUCLEIC ACID SEQUENCES IN AN UNPURIFIED SAMPLE

[75] Inventors: Nanibhushan Dattagupta, West Haven; Peter M. M. Rae, Hamden; Daniel U. Rabin, Branford; Edward D. Huguenel, Guilford, all of Conn.

[73] Assignee: Miles Inc., Elkhart, Ind.

[21] Appl. No.: 772,625

[22] Filed: Oct. 4, 1991

Related U.S. Application Data

[63] Continuation of Ser. No. 24,643, Mar. 19, 1987, abandoned, which is a continuation-in-part of Ser. No. 943,006, Dec. 19, 1986, abandoned, which is a continuation-in-part of Ser. No. 836,378, Mar. 5, 1986, abandoned.

[51] Int. Cl.$^5$ .............................................. C12Q 1/68
[52] U.S. Cl. ............................... 435/6; 536/24.3; 935/78; 435/29; 435/34; 435/35; 435/36; 436/63; 436/501
[58] Field of Search ................... 435/6, 91.1, 29, 34, 435/35, 36; 536/24.3; 935/78; 436/63, 501

[56] References Cited

U.S. PATENT DOCUMENTS

| | | | |
|---|---|---|---|
| 4,358,535 | 11/1982 | Falkow et al. | 435/6 |
| 4,395,486 | 7/1983 | Wilson et al. | 435/6 |
| 4,563,417 | 1/1986 | Albarella | 435/6 |
| 4,623,627 | 11/1986 | Huang et al. | 935/110 X |
| 4,689,295 | 8/1987 | Taber et al. | 435/6 |
| 4,737,454 | 4/1988 | Dattagupta et al. | 435/6 |
| 4,968,602 | 11/1990 | Dattagupta | 435/6 |

FOREIGN PATENT DOCUMENTS

| | | |
|---|---|---|
| 63879 | 11/1982 | European Pat. Off. . |
| 0130523 | 1/1985 | European Pat. Off. . |
| 0144914 | 6/1985 | European Pat. Off. . |
| 8301029 | 3/1984 | PCT Int'l Appl. . |

OTHER PUBLICATIONS

The New Genetics and Clinical Practice, D. J. Weatherall, The Nuffield Provincial Hospitals Trust, (1982), chapter 2.

Edward M. Rubin and Yeut Wai Kan, "A Simple Sensitive Prenatal Test for Hydrops Fetalis Caused by α—Thalassaemia", The Lancet, Jan. 12, 1985, pp. 75–77.

J. G. Wetmur, "Acceleration of DNA Renaturation Rates", Biopolymers, 14, 2517–2524, (1974).

R. M. Amasino, "Acceleration of Nucleic Acid Hybridization Rate by Polyethylene Glycol", Analytical Biochemistry, 152, 304–307, (1986).

M. Renz and C. Kurz, "A Colorimetric Method for DNA Hybridization", Nucleic Acids Res., 12, 3435–3444, (1984).

Dattagupta et al., Rapid Identification of Microorganisms by Nuclei Acid Hybridization After Labeling the Test Sample, Analytical Biochemistry, 177, 85–89 (1989).

Dattagupta et al., NucleicAcid Hydridization: A Rapid Method for the Diagnosis of Infectious Disease, Perspectives in Antiinfective Therapy, 241–247 (1988).

Bolden et al J Virology 16 (1975): 1584–1592.

Primary Examiner—Margaret Parr
Assistant Examiner—Kenneth R. Horlick
Attorney, Agent, or Firm—Sprung Horn Kramer & Woods

[57] ABSTRACT

A method for detecting (i) one or more microorganisms or (ii) nucleic acid sequences from a prokaryotic source or an eukaroytic source in an unpurified nucleic acid-containing test sample comprising (a) labeling the nucleic acids in the test sample, (b) contacting, under hybridization conditions, the labeled hybridizable nucleic acid and one or more immobilized hybridizable nucleic acid probes comprising (i) one or more known microorganisms or (ii) sequences from eukaroytic or prokaryotic sources, to form hybridized labeled nucleic acids, and (d) assaying for the hybridized nucleic acids by detecting the label. The method can be used to detect genetic disorders, e.g., sickle-cell anemia.

11 Claims, 2 Drawing Sheets

ASSAY FOR NUCLEIC ACID SEQUENCES IN AN UNPURIFIED SAMPLE

This application is a continuation of application Ser. No. 07/024,643, filed Mar. 11, 1987, abandoned, which is a continuation-in-part of application Ser. No. 06/943,006, filed Dec. 29, 1986, abandoned, which is a continuation-in-part of application Ser. No. 06/836,378, filed Mar. 5, 1986, abandoned.

BACKGROUND OF THE INVENTION

1. Field of the Invention

The present application relates to the detection and identification of microorganisms and the detection and identification of particular prokaryotic or eukaryotic DNA sources in a nucleic acid containing test sample.

Still further, the present invention relates to a method for the lysis of whole cells.

2. Background Information

A. The Detection of Microorganisms

The identification of species of microorganisms in a sample containing a mixture of microorganisms, by immobilizing the DNA from the sample and subjecting it to hybridization with a labelled specimen of species—specific DNA from a known microorganism and observing whether hybridization occurs between the immobilized DNA and the labelled specimen, has been disclosed in PCT patent application No. PCT/US83/01029.

The most efficient and sensitive method of detection of nucleic acids such as DNA after hybridization requires radioactively labeled DNA. The use of autoradiography and enzymes prolongs the assay time and requires experienced technicians.

U.S. Pat. No. 4,358,535 to Falkow et al describe infectious disease diagnosis using labeled nucleotide probes complementary to nucleic acid coding for a characteristic pathogen product.

B. The Detection of Specific Eukaryotic

The identification of specific sequence alteration in an eukaryotic nucleic acid sample by immobilizing the DNA from the sample and subjecting it to hybridization with a labeled oligonucleotide and observing whether hybridization occurs between the immobilized DNA and the labeled probe, has been described in U.S. patent application Ser. No. 815,974, filed Jan. 3, 1986, abandoned and U.S. patent application Ser. No. 845,221, filed Mar. 27, 1986, abandoned.

It is known that the expression of a specific gene determines the physical condition of a human being. Adult hemoglobin is a tetrameric association of two alpha and two beta subunits. During embryonic and fetal life, the alpha chains are associated with, successively, gamma and delta chains before the adult beta form predominates. The genes for alpha hemoglobin are located on human chromosome number 16 and the genes for gamma, delta and beta hemoglobin are tandemly linked on human chromosome 11. Hemoglobinopathies are heritable diseases that are the result of alterations in the structure of one or more of the hemoglobin genes. Many of the mutations have been characterized in considerable molecular detail and can range from single base pair changes to wholesale deletion of a gene family. For example, a change in the beta-globin gene coding sequence from GAG to GTG at the sixth amino acid position produces sickle-beta-globin and a homozygote can have a disease known as sickle cell anemia. Similarly deletion of particular sequences from alpha-globin or beta-globin genes can cause thalassemias. A recent survey, *The New Genetics and Clinical Practice*, D. J. Weatherall, The Nuffield Provincial Hospitals Trust, (1982), chapter 2 describes the frequency and clinical spectrum of genetic diseases.

Problems associated with genetic defects can be diagnosed by nucleic acid sequence information. The easiest way to detect such sequence information is to use the method of hybridization with a specific probe of a known sequence.

U.S. Pat. No. 4,395,486 to Wilson et al describe a method for the direct analysis of sickle cell anemia using a restriction endonuclease assay.

Edward M. Rubin and Yuet Wai Kan, "A Simple Sensitive Prenatal Test for Hydrops Fetalis Caused By δ-Thalassaemia", *The Lancet*, Jan. 12, 1985, pp. 75–77 describes a dot blot analysis to differentiate between the genotypes of homozygous alpha-thalassemia and those of the haemoglobin-H disease and alpha-thalassemia trait.

The most efficient and sensitive method of detection of nucleic acids, such as DNA, after hybridization requires radioactively labelled DNA. The use of autoradiography and enzymes prolongs the assay time and requires experienced technicians.

Recently, a non-radioactive method of labelling DNA was described by Ward et al, European Patent Application 63,879. Ward et al, use the method of nick translation to introduce biotinylated U (uracil) residues into DNA, replacing T (thymine). The biotin residue is then assayed with antibiotin antibody or an avidin-containing system. The detection in this case is quicker than autoradiography, but the nick translation method requires highly skilled personnel. Moreover, biotinylation using biotinylated UTP (uridine triphosphate) works only for thymine-containing polynucleotides. The use of other nucleoside triphosphates is very difficult because the chemical derivatization of A (adenine) or G (guanine) or C (cytosine) (containing $-NH_2$) with biotin requires the skills of trained organic chemists.

C. Effect of Nonionic Polymers on Hybridization

It has been shown by Wetmur (*Biopolymers*, 14, 2517–2524, (1974)) that anionic polymers such as dextran sulfate increase the rate of DNA-DNA hybridization in solution. It has also been shown that the heterogeneous phase hybridization rate can also be increased by dextran sulfate. U.S. Pat. No. 4,302,204 discloses the effect of charged polysaccharides on the rate of nucleic acid hybridization.

Recently Amasino (*Analytical Biochemistry*, 152, 304–307 (1986)) has shown that a neutral polymer like polyethylene glycol can increase the rate of DNA-RNA hybridization more than dextran sulfate under optimum conditions. Although polyethylene glycol (PEG) has been used before in the hybridization medium (e.g., Renz and Kurz, *Nucleic Acids Res.*, 12, 3435–3444 (1984)), no advantage was predicted over the use of dextran sulfate. Applicants have observed, to their surprise, that in the presence of 10% polyethylene glycol hybridization can be virtually finished in 15 minutes. Although Amasino supra has shown PEG is better than dextran sulfate as an accelerator, his labeled probe was single stranded RNA. In the case of the present invention, the labeled material is whole genomic sample DNA where both complementary strands are present in solution. When a polymer accelerates the rate of hybridization it should also help the reannealing in solution, and hence should reduce the efficiency of hybridization, instead of increasing it.

D. Cell Lysis

The present invention also provides a method for the efficient lysis of whole cells such that their DNA is released and made available for photochemical labeling. While eukaryotic cells derived from multicellular animals are easily lysed under relatively mild conditions, single cell eukaryotes and prokaryotes, especially Gram positive prokaryotes, are more difficult to lyse due to the complicated chemical nature and extent of cross-linking of their cell walls. Methods do exist for efficiently lysing these refractory organisms, either by chemical-enzymatic or physical means, but these methods are often complicated, time-consuming and inappropriate for preserving the integrity of DNA.

SUMMARY OF THE INVENTION

It is accordingly an object of the present invention to provide a rapid and convenient method for detection of one or more microorganisms or nucleic acid sequences from a prokaryotic source or an eukaryotic source in a nucleic acid-containing test sample.

It is another object of the invention to provide a method for a simultaneous assay for the presence of more than one nucleic acid sequence.

Another object of the invention involves direct labeling of the nucleic acid in the test sample.

A still further object of the invention is to use whole chromosomal nucleic acid as the probe and/or as the test sample.

Also the invention relates to the use of oligonucleotides as immobilized probes.

The invention further relates to the use of cloning vectors and their derivatives for use as immobilized probes.

The invention also concerns the use of polyethylene glycol as a hybridization accelerator.

Still further the invention is directed to preparing a cell lysate by contacting a cell with alkali.

These and other objects and advantages are realized in accordance with the present invention for a method of detecting (i) one or more microorganisms or (ii) nucleic acid sequences from a prokaryotic source or an eukaryotic source in a nucleic acid-containing test sample.

The method involves the following:
(a) labeling the nucleic acids, e.g., the nucleic acids of the organisms or cells or cell debris, in the test sample,
(b) contacting, under hybridization conditions, the labeled hybridizable sample nucleic acid and one or more immobilized hybridizable (e.g., single-stranded) nucleic acid (e.g., DNA) probes comprising of (i) one or more known microorganisms or (ii) nucleic acid sequences from eukaryotic or prokaryotic sources, to form hybridized labeled nucleic acids and
(c) assaying for the hybridized nucleic acids by detecting the label.

The hybridizable nucleic acid can be whole genomic nucleic acid or a fragment thereof, e.g., an oligonucleotide.

In step (a), the nucleic acids can be labeled directly in the test sample. In step (a), in such direct labeling, cells of the test sample can be lysed and then a labeling reagent can be added, whereby to label the nucleic acid.

The method further comprises denaturing the labeled nucleic acids from step (a) to form labeled denatured nucleic acids.

According to the invention, a labeled nucleic acid test sample is contacted simultaneously with several different types of nucleic acid, e.g., DNA, probes for hybridization. The nucleic acid test sample is labeled and hybridized with several unlabeled immobilized probes. The positions of the probes are fixed, and the labeled probe detected after hybridization will indicate that the test sample carries a nucleic acid sequence complementary to the corresponding probe.

Nucleic acid probes for several microbiological systems or for different alleles of one or more genes can be immobilized separately on a solid support, for example, nitrocellulose paper. The test sample nucleic acids are labeled and remain in solution. The solid material containing the immobilized probe is brought in contact with the labeled test nucleic acid solution under hybridization conditions. The solid material is washed free of unhybridized nucleic acid and the label is assayed. The presence of the label with one or more of the probes indicates that the test sample contains nucleic acids substantially complementary to those probes and hence originate, for example, from an infection by particular microbiological systems.

Labeling can be accomplished in a whole living cell or a cell lysate, and can be non-isotopic. The nucleic acid can be used for hybridization without further purification.

The present invention also concerns specific lysis conditions to release nucleic acids from both gram positive and gram negative bacteria.

The present invention also relates to a hybridization medium which accelerates the process of hybridization. A hybridization accelerator according to the present invention is polyethylene glycol.

The present invention further concerns a kit for detecting (i) one or more microorganisms or (ii) nucleic acid sequences from a prokaryotic source or an eukaryotic source in a nucleic acid-containing test sample comprising
(a) a support solid containing hybridizable, e.g., single-stranded, nucleic acid, e.g., DNA or an oligonucleotide, of (i) said one or more known microorganisms or (ii) said sequences from eukaryotic or prokaryotic sources immobilized thereon, e.g., a strip containing dots or spots of known microorganisms or eukaryotes or prokaryotes,
(b) a reagent for labeling the nucleic acid of the test sample,
(c) a reagent for releasing and denaturing nucleic acid, e.g., DNA, in the test sample, and
(d) hybridization reagents.

For chemiluminescence detection of the hybridized nucleic acid, the kit would further comprise a reagent for chemiluminescent detection.

In the above described kit, the reagent for labeling is given hereinbelow in a discussion on labels.

Reagents for releasing and denaturing DNA include sodium hydroxide and lysing agents such as detergents and lysozymes.

Typical hybridization reagents includes a mixture of sodium chloride, sodium citrate, SDS (sodium dodecyl sulfate), bovine serum albumin, nonfat milk or dextran sulfate and optionally formamide.

The present invention further concerns a method of hybridization comprising contacting two complementary single stranded nucleic acids under hybridization conditions, at least one of which is immobilized wherein polyethylene glycol is added.

DETAILED DESCRIPTION OF THE INVENTION

Figure 1:
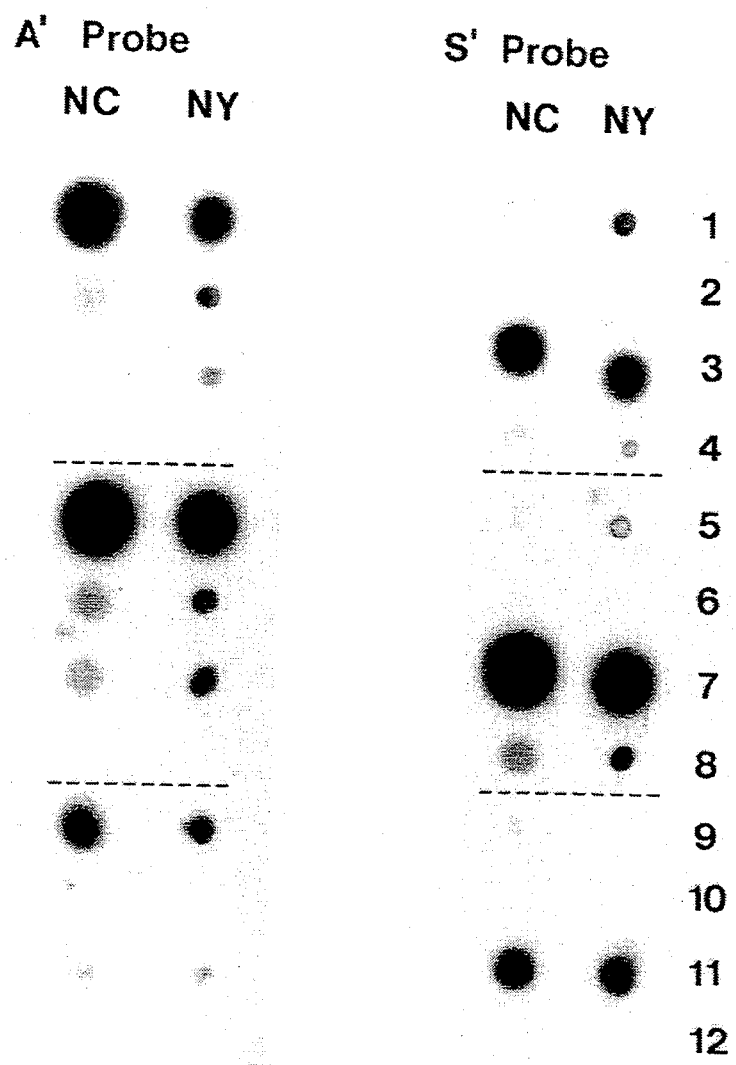
FIG. 1 is an autoradiograph of results of immobilization of an oligonucleotide sequence specific for hemoglobin mutation.

The test sample in the present invention includes body fluids, e.g., urine, blood, semen, cerebrospinal fluid, pus, amniotic fluid, tears, or semisolid or fluid discharge, e.g., sputum, saliva, lung aspirate, vaginal or urethal discharge, stool or solid tissue samples, such as a biopsy or chorionic villispecimens. Test samples also include samples collected with swabs from the skin, genitalia, or throat.

All these test samples can be used for hybridization diagnosis after labeling the nucleic acids of the sample. The labeling can be accomplished without any processing of the sample. As for example, a urine sample (suspected of bacterial infections) can be labeled without centrifugation, filtration or dialysis. The cells in the samples can be lysed without any separation step. It is surprising that a nucleic acid labeling reaction takes place in such a complex mixture as a clinical sample.

The nucleic acid is preferably labeled by means of photochemistry, employing a photoreactive DNA-binding furocoumarin or a phenanthridine compound to link the nucleic acid to a label which can be "read" or assayed in conventional manner, including fluorescence detections. The end product is thus a labeled nucleic acid comprising (a) a nucleic acid component, (b) an intercalator or other DNA-binding ligand photochemically linked to the nucleic acid component, and (c) a label chemically linked to (b).

The photochemical method provides more favorable reaction conditions than the usual chemical coupling method for biochemically sensitive substances. The intercalator and label can first be coupled and then photoreacted with the nucleic acid, or the nucleic acid can first be photoreacted with the intercalator and then coupled to the label.

A general scheme for coupling a nucleic acid, exemplified by double-stranded DNA, to apply a label, is as follows:

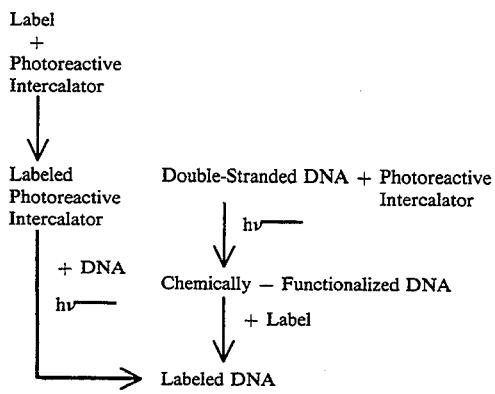

Where the hybridizable portion of the nucleic acid is in a double stranded form, such portion is then denatured to yield a hybridizable single stranded portion. Alternatively, where the labeled DNA comprises the hybridizable portion already in single stranded form, such denaturation can be avoided if desired. Alternatively, double stranded DNA can be labeled by the approach of the present invention after hybridization has occurred using a hybridization format which generates double stranded DNA only in the presence of the sequence to be detected.

To produce specific and efficient photochemical products, it is desirable that the nucleic acid component and the photoreactive intercalator compound be allowed to react in the dark in a specific manner.

For coupling to DNA, aminomethyl psoralen, aminomethyl angelicin and amino alkyl ethidium or methidium azides are particularly useful compounds. They bind to double-stranded DNA and only the complex yields photoadduct. In the case where labeled double-stranded DNA must be denatured in order to yield a hybridizable single stranded region, conditions are employed so that simultaneous interaction of two strands of DNA with a single photoadduct is prevented. It is necessary that the frequency of modification along a hybridizable single stranded portion of the nucleic acid not be so great as to substantially prevent hybridization, and accordingly there preferably will be not more than one site of modification per 25, more usually 50, and preferably 100, nucleotide bases. Angelicin derivatives are superior to psoralen compounds for monoadduct formation. If a single-stranded DNA nucleic acid is covalently attached to some extra double-stranded DNA, use of phenanthridium and psoralen compounds is desirable since these compounds interact specifically to double-stranded DNA in the dark. The chemistry for the synthesis of the coupled reagents to modify nucleic acids for labeling, described more fully hereinbelow, is similar for all cases.

The nucleic acid component can be single or double stranded DNA or RNA or fragments thereof such as are produced by restriction enzymes or even relatively short oligomers.

The DNA-binding ligands of the present invention used to link the nucleic acid component to the label can be any suitable photoreactive form of known DNA-binding ligands. Particularly preferred DNA-binding ligands are intercalator compounds such as the furocoumarins, e.g., angelicin (isopsoralen) or psoralen or derivatives thereof which photochemically will react with nucleic acids, e.g., 4'-aminomethyl-4,5'-dimethyl angelicin, 4'-aminomethyl-trioxsalen (4'aminomethyl-4,5',8-trimethyl-psoralen), 3-carboxy-5- or -8-amino- or-hydroxy-psoralen, as well as mono- or bis-azido aminoalkyl methidium or ethidium compounds.

Particularly useful photoreactive forms of intercalating agents are the azidointercalators. Their reactive nitrenes are readily generated at long wavelength ultraviolet or visible light and the nitrenes of arylazides prefer insertion reactions over their rearrangement products (see White et al, *Methods in Enzymol.*, 46, 644 (1977)). Representative intercalating agents include azidoacridine, ethidium monoazide, ethidium diazide, ethidium dimer azide (Mitchell et at, *JACS*, 104, 4265 (1982)), 4-azido-7-chloroquinoline, and 2-azidofluorene. A specific nucleic acid binding azido compound has been described by Forster et al, *Nucleic Acid Res.*, 13, (1985), 745. The structure of such compound is as follows:

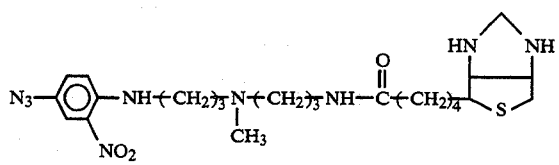

Other useful photoreactable intercalators are the furocoumarins which form (2+2) cycloadducts with pyrimidine residues. Alkylating agents can also be used such as bis-chloroethylamines and epoxides or aziridines, e.g., aflatoxins, polycyclic hydrocarbon epoxides, mitomycin and norphillin A.

Nonlimiting examples of intercalator compounds for use in the present invention include acridine dyes, phenanthridines, phenazines, furocoumarins, phenothiazines and quinolines.

The label which is linked to the nucleic acid component according to the present invention can be any chemical group or residue having a detectable physical or chemical property, i.e., labeling can be conducted by chemical reaction or physical adsorption. The label will bear a functional chemical group to enable it to be chemically linked to the intercalator compound. Such labeling materials have been well developed in the field of immunoassays and in general most any label useful in such methods can be applied to the present invention. Particularly useful are enzymatically active groups, such as enzymes (see *Clin. Chem.*, (1976), 22, 1243), enzyme substrates (see British Pat. Spec. 1,548,741), coenzymes (see U.S. Pat. Nos. 4,230,797 and 4,238,565) and enzyme inhibitors (see U.S. Pat. No. 4,134,792; fluorescers (see *Clin. Chem.*, (1979), 25, 353), and chromophores including phycobiliproteins; luminescers such as chemiluminescers and bioluminescers (see *Clin. Chem.*, (1979), 25, 512, and ibid, 1531); specifically bindable ligands, i.e., protein binding ligands; and residues comprising radioisotopes such as $^3H$, $^{35}S$, $^{32}P$, $^{125}I$, and $^{14}C$. Such labels are detected on the basis of their own physical properties (e.g., fluorescers, chromophores and radioisotopes) or their reactive or binding properties (e.g., enzymes, substrates, coenzymes and inhibitors). For example, a cofactor-labeled nucleic acid can be detected by adding the enzyme for which the label is a cofactor and a substrate for the enzyme. A hapten or ligand (e.g., biotin) labeled nucleic acid can be detected by adding an antibody or an antibody pigment to the hapten or a protein (e.g., avidin) which binds the ligand, tagged with a detectable molecule. An antigen can also be used as a label. Such detectable molecule can be some molecule with a measurable physical property (e.g, fluorescence or absorbance) or a participant in an enzyme reaction (e.g., see above list). For example, one can use an enzyme which acts upon a substrate to generate a product with measurable physical property. Examples of the latter include, but are not limited to, beta-galactosidase, alkaline phosphatase, papain and peroxidase. For in situ hybridization studies, ideally the final product is water insoluble. Other labels, e.g., dyes, will be evident to one having ordinary skill in the art.

The label will be linked to the intercalator compound, e.g., acridine dyes, phenanthridines, phenazines, furocoumarins, phenothiazines and quinolines, by direct chemical linkage such as involving covalent bonds, or by indirect linkage such as by the incorporation of the label in a microcapsule or liposome which in turn is linked to the intercalator compound. Methods by which the label is linked to the intercalator compounds are essentially known in the art and any convenient method can be used to perform the present invention.

Advantageously, the intercalator compound is first combined with label chemically and thereafter combined with the nucleic acid component. For example, since biotin carries a carboxyl group, it can be combined with a furocoumarin by way of amide or ester formation without interfering with the photochemical reactivity of the furocoumarin or the biological activity of the biotin, e.g.,

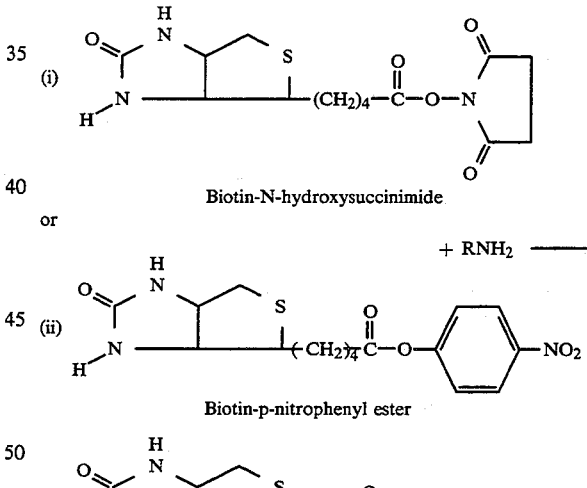

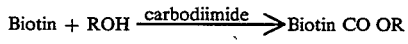

By way of example

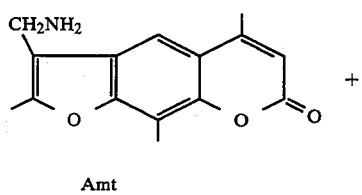

Amt

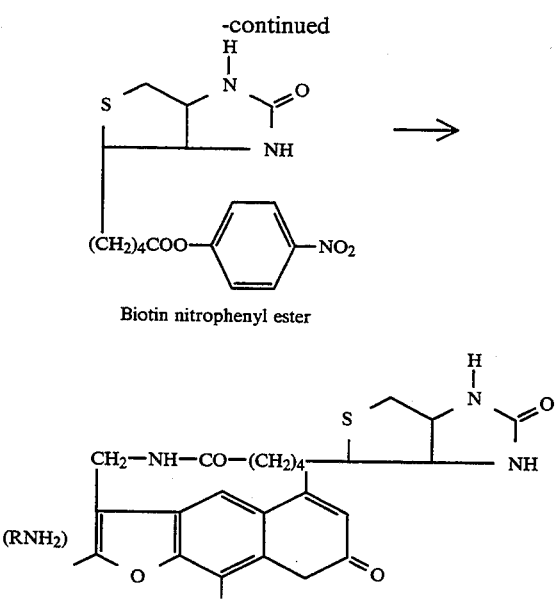

Other aminomethylangelicin, psoralen and phenanthridium derivatives can be similarly reacted, as can phenanthridium halides and derivatives thereof such as aminopropyl methidium chloride, i.e.,

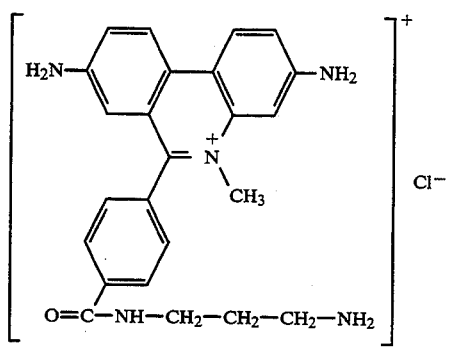

(see Hertzberg et al, *J. Amer. Chem. Soc.*, 104, 313 (1982)).

Alternatively, a bifunctional reagent such as dithiobis succinimidyl propionate or 1,4-butanediol diglycidyl ether can be used directly to couple the photochemically reactive molecule with the label where the reactants have alkyl amino residues, again in a known manner with regard to solvents, proportions and reaction conditions. Certain bifunctional reagents, possibly glutraidehyde may not be suitabie because, while they couple, they may modify nucleic acid and thus interfere with the assay. Routine precautions can be taken to prevent such difficulties.

The particular sequence used in making the labeled nucleic acid can be varied. Thus, for example, an amino-substituted psoralen can first be photochemically coupled with a nucleic acid, the product having pendant amino groups by which it can be coupled to the label, i.e., labeling can be carried out by photochemically reacting a DNA binding ligand with the nucleic acid in the test sample. Alternatively, the psoralen can first be coupled to a label such as an enzyme and then to the nucleic acid.

As described in U.S. patent application Ser. No. 690,336, filed Jan. 10, 1985, abandoned, the present invention also encompasses a labeled nucleic acid comprising (a) a nucleic acid component, (b) a nucleic acid-binding ligand photochemically linked to the nucleic acid component, (c) a label and (d) a spacer chemically linking (b) and (c).

Advantageously, the spacer includes a chain of up to about 40 atoms, preferably about 2 to 20 atoms, selected from the group consisting of carbon, oxygen, nitrogen and sulfur.

Such spacer may be the polyfunctional radical of a member selected from the group consisting of peptide, hydrocarbon, polyalcohol, polyether, polyamine, polyimine and carbohydrate, e.g., -glycyl-glycyl-glycyl- or other oligopeptide, carbonyl dipeptides, and omega-amino-alkane-carbonyl radical such as —NH(CH$_2$)$_5$—CO—, a spermine or spermidine radical, an alpha, omega-alkanediamine radical such as —NH—(CH$_2$)$_6$—NH or —HN—CH$_2$—CH$_2$—NH, or the like. Sugar, polyethylene oxide radicals, glyceryl, pentaerythritol, and like radicals can also serve as the spacers.

These spacers can be directly linked to the nucleic acid-binding ligand and/or the label or the linkages may include a divalent radical of a coupler such as dithiobis succinimidyl propionate, 1,4-butanediol diglycidyl ether, a diisocyanate, carbodiimide, glyoxal, glutaraldehyde, or the like.

The spacer can be incorporated at any stage of the process of making the probe defined hereinabove. Thus, the sequence can be any of the following:

a+b+d+c, b+d+c+a, d+c+b+a, b+d+a+c, etc.

The conditions for the individual steps are well known in chemistry.

If the label is an enzyme, for example, the product will ultimately be placed on a suitable medium and the extent of catalysis will be determined. Thus, if the enzyme is a phosphatase, the medium could contain nitrophenyl phosphate and one would monitor the amount of nitrophenol generated by observing the color. If the enzyme is a beta-galactosidase, the medium can contain o-nitro- phenyl-D-galacto-pyranoside which also will liberate nitrophenol.

The labeled nucleic acid of the present invention is applicable to all conventional hybridization assay formats, and in general to any format that is possible based on formation of a hybridization product or aggregate comprising the labeled nucleic acid. In particular, the unique labeled nucleic acid of the present invention can be used in solution and solid-phase hybridization formats, including, in the latter case, formats involving immobilization of either sample or probe nucleic acids and sandwich formats.

The nucleic acid probe will comprise at least one hybridizable, e.g., single-stranded, base sequence substantially complementary to or homologous with the sequence to be detected. However, such base sequence need not be a single continuous polynucleotide segment, but can be comprised of two or more individual segments interrupted by nonhomologous sequences. These nonhomologous sequences can be linear or they can be self-complementary and form hairpin loops. In addition, the homologous region of the probe can be flanked at the 3'- and 5' termini by nonhomologous sequences, such as those comprising the DNA or RNA or a vector into which the homologous sequence had been inserted for propagation. In either instance, the probe as presented as an analytical reagent will exhibit detectable hybridization at one or more points with sample nucleic acids of interest. Linear or circular hybridizable, e.g., single-stranded polynucleotides can be used as the probe element, with major or minor portions being duplexed with a complementary polynucleotide strand or strands, provided that the critical homologous segment or segments are in single-stranded form and available for hybridization with sample DNA or RNA. Useful probes include linear or circular probes wherein the homologous probe sequence is in essentially only single-stranded form (see particularly, Hu and Messing, *Gene*, 17:271 (1982)).

The nucleic acid probe of the present invention can be used in any conventional hybridization technique. As improvements are made and conceptually new formats are developed, such can be readily applied to the present probes. Conventional hybridization formats which are particularly useful include those wherein the sample nucleic acids or the polynucleotide probe is immobilized on a solid support (solid-phase hybridization) and those wherein the polynucleotide species are all in solution (solution hybridization).

In solid-phase hybridization formats, one of the polynucleotide species participating in hybridization is fixed in an appropriate manner in its single-stranded form to a solid support. Useful solid supports are well known in the art and include those which bind nucleic acids either covalently or noncovalently. Noncovalent supports which are generally understood to involve hydrophobic bonding include naturally occurring and synthetic polymeric materials, such as nitrocellulose, derivatized nylon and fluorinated polyhydrocarbons, in a variety of forms such as filters, beads or solid sheets. Covalent binding supports (in the form of filters, beads or solid sheets, just to mention a few) are also useful and comprise materials having chemically reactive groups or groups, such as dichlorotriazine, diazobenzyloxymethyl, and the like, which can be activated for binding to polynucleotides.

It is well known that noncovalent immobilization of an oligonucleotide is ineffective on a solid support, for example, on nitrocellulose paper. The present invention also describes novel methods of oligonucleotide immobilization. This is achieved by phosphorylation of an oligonucleotide by a polynucleotide kinase or by ligation of the 5'-phosphorylated oligonucleotide to produce multi-oligonucleotide molecules capable of immobilization. The conditions for kinase and ligation reaction have been described in standard text books, e.g., *Molecular Cloning*, T. Manjarls, E. F. Fritsch and J. Sambrook, Cold Spring Harbor Laboratory, (1982), pages 1-123.

A typical solid-phase hybridization technique begins with immobilization of sample nucleic acids onto the support in single-stranded form. This initial step essentially prevents reannealing of complementary strands from the sample and can be used as a means for concentrating sample material on the support for enhanced detectability. The polynucleotide probe is then contacted with the support and hybridization detected by measurement of the label as described herein. The solid support provides a convenient means for separating labeled probe which has hybridized to the sequence to be detected from that which has not hybridized.

Another method of interest is the sandwich hybridization technique wherein one of two mutually exclusive fragments of the homologous sequence of the probe is immobilized and the other is labelled. The presence of the polynucleotide sequence of interest results in dual hybridization to the immobilized and labelled probe segments. See *Methods in Enzymology*, 65:468 (1980) and *Gene*, 21:77-85 (1983) for further details.

For the present invention, the immobile phase of the hybridization system can be a series or matrix of spots of known kinds and/or dilutions of denatured DNA. This is most simply prepared by pipetting appropriate small volumes of native DNA onto a dry nitrocellulose or nylon sheet, floating the sheet on a sodium hydroxide solution to denature the DNA, rinsing the sheet in a neutralizing solution, then baking the sheet to fix the DNA. Before DNA:DNA hybridization, the sheet is usually treated with a solution that inhibits non-specific binding of added DNA during hybridization.

This invention involves the labeling of whole genomic DNA, whole nucleic acids present in cells, whole cell lysate, or unlysed whole cells. Once the labeled material is prepared, it can be used for the detection, i.e., the presence or absence of certain specific genomic sequences by specific nucleic acid hybridization assays.

One method according to the invention involves the separation of cells from a human sample or the human sample directly is treated by mixing with a photochemically reactive nucleic acid binding intercalating ligand. The mixture is incubated depending on the type of the sample. If the sample is lysed cells or nucleic acids, it is incubated for a period between a few seconds to five minutes and when whole cells or partially lysed cells are used, incubation between two minutes to two hours is employed. After the mixing and incubation, the whole sample mixture is irradiated at a particular wavelength for the covalent interaction between the photochemically reactive DNA binding ligand and the test sample. Then this labeled material is hybridized under specific hybridization conditions with a specific probe.

After the hybridization, the unreacted unhybridized labeled test sample is removed by washing. After the washing, the hybrid is detected through the label carried by the test sample, which is specifically hybridized with a specific probe.

The present invention is surprising since in a human genomic sample the amount of a single copy gene is very low, for example, if a restriction fragment of one thousand base pairs is the region of hybridization, the frequency of such sequence in the whole human genomic sample is one in a million. This conclusion has been derived by assuming from the literature that a human genomic sample has $3 \times 10^9$ base pairs and 1000 base pairs will be 1/3,000,000 of that number. Automatically, in a sample of human DNA containing approximately five to ten micrograms of nucleic acids, only 5 to 10 picogram of the corresponding sequences is available and labeling the vast majority of the non-specific DNA should produce more background than the true signal. But after the reaction, it is surprising to observe that the results are not only specific, but also of unexpected higher sensitivity.

Without wishing to be bound by any particular theory of operability, the reason for the unexpected sensitivity may be due to the formation of a network of non-specific nucleic acid hybrids bound to the specific hybrid, thus amplifying the amount of the signal. As has been shown in a typical example, a 19 nucleotide long specific sequence containing plasmid is immobilized and hybridized with 5 microgram equivalent of a test sample which is labeled photochemically and one detects very easily the signal resulted from such hybrid. This could not have been accomplished by any other technique because of the problems associated with the labeling method.

The present invention relates to a novel hybridization technique where probes are immobilized and an eukaryotic nucleic acid sample is labeled and hybridized with immobilized unlabeled probe. A surprising characteristic of the invention is the ability to detect simple or multiple copy gene defects by labeling the test sample. Since there is no requirement for an excess of labeled hybridizing sequence, the present method is more specific. In the present invention, simultaneous detection of different gene defects can be easily carried out by immobilizing specific probes.

For example, using the present invention, one can immobilize oligonucleotide probes specific for genetic defects related to hemoglobinopathines, such as sickle cell anemia and alpha-thalassemias on a sheet of nitrocellulose paper, label the test sample and hybridize the labeled test sample with the immobilized probes. It is surprising that partially purified or unpurified nucleic acid samples (cell lysate or whole cell) can be photochemically labeled with sensitive molecules without affecting the specific hybridizability.

The oligonucleotide can be cloned in cloning vectors, e.g., M 13, PUC 19 and PBR and accordingly the vector containing the oligonucleotide acts as the probe.

The present invention is also directed to detecting eukaroytes (protists) in samples from higher organisms, such as animals or humans.

Eukaroytes include algae, protozoa, fungi and slime molds.

The term "algae" refers in general to chlorophyll-containing protists, descriptions of which are found in G. M. Smith, *Cryptogamic Botany,* 2nd ed. Vol. 1, *Algae and Fungi,* McGraw-Hill, (1955).

Eukaryotic sequences according to the present invention includes all disease sequences except for bacteria and viruses. Accordingly, genetic diseases, for example, would also be embraced by the present invention. Non-limiting examples of such genetic diseases are as follows:

| Area Affected | Diseases |
| --- | --- |
| Metabolism | Acute intermittent porphyria |
| | Variegate porphyria |
| | alpha$_1$-antitrypsin deficiency |
| | Cystic fibrosis |
| | Phenylketonuria |
| | Tay-Sachs disease |
| | Mucopolysaccharidosis I |
| | Mucopolysaccharidosis II |
| | Galactosaemia |
| | Homocystinuria |
| | Cystinuria |
| | Metachromic leucodystrophy |
| Nervous System | Huntington's chorea |
| | Neurofibromatosis |
| | Myotonic dystrophy |
| | Tuberous sclerosis |

-continued

| Area Affected | Diseases |
| --- | --- |
| | Neurogenic muscular atrophies |
| Blood | Sickle-cell anaemia |
| | Beta-thalassaemia |
| | Congenital spherocytosis |
| | Haemophilia A |
| Bowel | Polyposis coli |
| Kidney | Polycystic disease |
| Eyes | Dominant blindness |
| | Retinoblastoma |
| Ears | Dominant early childhood deafness |
| | Dominant otosclerosis |
| Circulation | Monogenic hypercholesterolaemia |
| Blood | Congenital spherocytosis |
| Teeth | Dentinogenisis imperfecta |
| | Amelogenisis imperfecta |
| Skeleton | Diaphysial aclasia |
| | Thanatophoric dwarfism |
| | Osteogenes imperfecta |
| | Marfan syndrome |
| | Achondroplasia |
| | Ehlers-Danlos syndrome |
| | Osteopetrosis tarda |
| | Cleft lip/palate |
| Skin | Ichthyosis |
| Locomotor | Muscular dystrophy |

A nucleic acid probe in accordance with the present invention is a sequence which can determine the sequence of a test sample. The probes are usually DNA, RNA, mixed copolymers of ribo- and deoxyribonucleic acids, oligonucleotides containing ribonucleotides or deoxyribonucleotide residues or their modified forms. The sequence of such a probe should be complementary to the test sequence. The extent of complementary properties will determine the stability of the double helix formed after hybridization. The probe can also have covalently linked non-complementary nucleic acids. They can serve as the sites of the labeling reaction.

The nucleic acid is preferably labeled by means of photochemistry, employing a photoreactive DNA-binding furocoumarin or a phenanthridine compound to link the nucleic acid to a label which can be "read" or assayed in conventional manner, including fluorescence detection.

One use of the present invention is the identification of bacterial species in biological fluids. In one application, samples of urine from subjects having or suspected of having urinary tract infections can provide material for the preparation of labeled DNA(s) or RNAs, while a solid support strip, e.g., made of nitrocellulose or nylon, can contain individual dots or spots of known amounts of denatured purified DNA from each of the several bacteria likely to be responsible for infection.

The format of labeled unknown and unlabeled probes, which is the converse of standard schemes, allows one to identify among a number of possibilities the species of organism in a sample with only a single labeling. It also allows simultaneous determination of the presence of more than one distinguishable bacterial species in a sample (assuming no DNA in a mixture is discriminated against in the labeling procedure). However, it does not allow in a simple way, better than an estimate of the amount of DNA (and, therefore, the concentration of bacteria) in a mixed sample. For such quantitation, sample DNA is immobilized in a series of dilution spots along with spots of standard DNA, and probe DNAs are labeled.

A urinary tract infection is almost always due to monoclonal growth of one of the following half dozen kinds of microorganism: Escherichia coli (60–90% of UTI), Proteus spp. (5–20% of UTI), Klebsiella spp (3–10% of UTI), Staphylococcus spp. (4–20% of UTI), Streptococcus spp. (2–5% of UTI). Pseudomonas and some other gram negative rods together account for a low percentage of UTI. A common contaminant of urine samples that is a marker of improper sample collection is Lactobacillus.

The concentration of bacteria in a urine sample that defines an infection is about $10^5$ per milliliter.

The format for an unlabeled probe hybridization system applicable to urinary tract infections is to have a matrix of DNAs from the above list of species, denatured and immobilized on a support such as nitrocellulose, and in a range of amounts appropriate for concentrations of bacterial DNAs that can be expected in samples of labelled unknown.

Standard hybridization with biotinylated whole genome DNA probes takes place in 5–10 ml, at a probe concentration of about 0.1 $\mu$g/ml; hybridization of probe to a spot containing about 10 ng denatured DNA is readily detectable. There is about 5 fg of DNA per bacterial cell, so that for a sample to contain 1 $\mu$g of labeled DNA, it is necessary to collect $2 \times 10^8$ bacteria. If an infection produces urine having approximately $10^5$ bacteria/ml, then bacterial DNA to be labeled from a sample is concentrated from 2000 ml. If more than 10 ng unlabeled probe DNA is immobilized in a dot, for example, 100 ng or 1 $\mu$g, or if the hybridization volume is reduced, then the volume of urine required for the preparation of labeled unknown is approximately a few tenths of a ml.

A strip of dots containing immobilized, denatured, unlabelled probe DNAs could have the following configuration:

|  | 1 $\mu$g | 10 ng | 100 pg |
|---|---|---|---|
| Escherichia | o | o | o |
| Proteus | o | o | o |
| Klebsiella | o | o | o |
| Staphylococcus | o | o | o |
| Streptococcus | o | o | o |
| Pseudomonas | o | o | o |
| Lactobacillus | o | o | o |

This procedure involves the labeling of DNA or RNA in a crude cell lysate. Ideally, preparation of labeled sample DNA or RNA will accommodate the following points:

(1) bacteria will be concentrated from a fluid sample by centrifugation or filtration;
(2) bacteria will be lysed under conditions sufficient to release nucleic acids from the most refractory of the organisms of interest;
(3) the labeling protocol will not require purification of labeled nucleic acids from unincorporated precursors, nor the purification of nucleic acids prior to labeling;
(4) the labeling protocol will be sufficiently specific for DNA and/or RNA that proteins, lipids and polysaccharides in the preparation will not interfere with hybridization nor read-out.

In the present invention, there is provided a method for efficiently and rapidly lysing whole cells, including Gram positive bacteria. The method involves contacting cells, e.g., whole cells, with an alkali, e.g., sodium or potassium hydroxide solution in a concentration of 0.1 to 1.6 Normal.

The important features of the present lysis protocol are its relative simplicity and speed. It employs a con, non chemical that requires no special storage conditions and it lyses even Gram positive organisms with high efficiency, while preserving the properties of the DNA that are important for subsequent steps in the photochemical labeling process.

For the present invention, the immobile phase of the hybridization system can be a series or matrix of spots of known kinds and/or dilutions of denatured DNA. This is most simply prepared by pipetting appropriate small volumes of native DNA or oligonucleotides onto a dry nitrocellulose or nylon sheet, floating the sheet on a sodium hydroxide solution to denature the DNA, rinsing the sheet in a neutralizing solution, then baking the sheet to fix the DNA. Before DNA:DNA hybridization, the sheet is usually treated with a solution that inhibits non-specific binding of added DNA during hybridization.

The invention will be further described in the following non-limiting examples wherein parts are by weight unless otherwise expressed.

EXAMPLES

Example 1: Preparation of Labeling Compound

The preparation of the labeling compound required 1-amino-17-N-(Biotinylamido)-3,6,9,12,15 pentaoxaheptadecane. This compound was prepared in the following four steps:

(a) 3,6,9,12,15 pentaoxaheptadecane 1,17-diol ditosylate was synthesized.
(b) 1,17-dipthalimido derivative of 3,6,9,12, 15 pentaoxaheptadecane was prepared.
(c) 1,17-diamino derivative of 3,6,9,12,15 pentaoxaheptadecane was prepared.
(d) 1-amino, 17-biotinylamido derivative of 3,6,9,12,15 pentaoxaheptadecane was prepared.

Example 1(a): Preparation of 3,6,9,12,15-Pentaoxaheptadecane-1,17-diol Ditosylate To a stirred solution containing 50 g of hexaethylene glycol (0.177 mol) and 64 ml of triethylamine (39.36 g, 0.389 mol) in 400 ml of $CH_2Cl_2$ at 0° C. was added dropwise a solution containing 73.91 g of p-toluenesulfonyl chloride (0.389 mol) in 400 ml of $CH_2Cl_2$ over a 2.5 hour period. The reaction mixture was then stirred for one hour at 0° C. and then heated to ambient temperature for 44 hours. The mixture was then filtered and the filtrate was concentrated in vacuo. The resulting heterogeneous residue was suspended in 500 ml of ethyl acetate and filtered. The filtrate was then concentrated in vacuo to a yellow oil which was triturated eight times with 250 ml portions of warm hexane to remove unreacted p-toluenesulfonyl chloride. The resulting oil was then concentrated under high vacuum to yield 108.12 g of a yellow oil (quantitative yield).

Analysis: Calculated for $C_{26}H_{38}O_{11}S_2$ Calc.: C, 52.87; H, 6.48. found: C, 52.56; H, 6.39.

PMR: (60 MHz, $CDCl_3$) $\delta$: 2.45 (s, 6H); 3.4–3.8 (m, 20H); 4.2 (m, 4H); 7.8 (AB quartet, J=8Hz, 8H).

IR: (neat) $cm^{-1}$: 2870, 1610, 1360, 1185, 1105, 1020 930, 830, 785, 670.

Example 1(b): Preparation of 1,17-Diphthalimido3,6,9,12,15-pentaoxaheptadecane A stirred suspension containing 108 g of 3,6,9,12,15-pentaoxaheptadecane-1,17-diol ditosylate (0.183 mol), 74–57 g of potassium phthalimide (0.403 mol), and 700 ml of dimethylacetamide was heated at 160°–170° C. for 2 hours and was then cooled to room temperature. The precipitate was filtered and washed with water and acetone to yield 53.05 g of product as a white powder which was dried at 55° C. (0.1 mm). mp 124°–126° C.

A second crop of product was obtained from the dimethylacetamide filtrate by evaporation in vacuo and the resulting precipitate with was successively washed ethyl acetate, water, and acetone. The resulting white powder was dried at 55° C. (0.1 mm) to yield an additional 9.7 g of product. mp 124.5°–126.5° C. The combined yield of product was 62.82 g (68% yield).

Analysis: (For first crop) Calculated for $C_{28}H_{32}N_2O_9 \cdot \frac{1}{2}H_2O$ Calc.: C, 61.19; H, 6.05; N, 5.09. found: C, 61.08; H. 6.15; N, 5.05.

(For second crop) Calculated for $C_{28}H_{32}N_2O_9$ Calc.: C, 62.21; H, 5.97; N, 5.18. found: C, 61.78; H, 6.15; N, 5.13.

PMR: (60 MHz, dmso-$d_6$) δ: 3.5 (s, 8H); 3.6 (s, 8H); 3.8 (bt, J=3Hz, 8H): 8.1 ( s, 8H).

IR: (KBr) cm$^{-1}$: 2890, 1785, 1730, 1400, 1100, 735.

Example 1(c): Preparation of 1,17-Diamino-3,6,9,12,15-Pentaoxaheptadecane

A solution containing 60 g of 1,17-diphthalimido-3,6,9,12,15-pentaoxaheptadecane (0.118 mol), 14.8 g of hydrazine hydrate (0.296 mol), and 500 ml of ethanol were heated with mechanical stirring in a 100° C. oil bath for three hours. The mixture was then cooled and filtered. The resultant filter cake was washed four times with 300 ml portions of ethanol. The combined filtrates were concentrated to yield 32.35 g of a yellow opaque glassy oil. The evaporative distillation at 150°–200° C. (0.01 mm) gave 22.82 g of a light yellow oil (69% yield). lit. b.p. 175°–177° C. (0.07 mm).

PMR: (60 MHz, CDCl$_3$) δ: 1.77 (s, 4H, NH$_2$); 2.85 (t, J=5Hz, 4H); 3.53 (t, J=5Hz, 4H); 3.67 (m, 16H).

(CHCl$_3$) cm$^{-1}$: 3640, 3360, 2860, 1640, 1585, 1460, 1350, 1250, 1100, 945, 920, 870.

Mass Spectrum: (EI) m/e=281.2 (0.1%, M+1).

(FAB) m/e=281.2 (100%, M+1).

Analysis: For $C_{12}H_{28}N_2O_5 \cdot \frac{1}{2}H_2O$ Calc.: C, 49.80, H, 10.10; N, 9.68. found: C, 50.36; H, 9.58; N, 9.38.

Literature Reference: W. Kern, S. Iwabachi, H. Sato and V. Bohmer, *Makrol. Chem.*, 180, 2539 (1979).

Example 1(d): Preparation of 1-Amino-17-N-(Biotinylamido)-3,6,9,12,15-pentaoxaheptadecane A solution containing 7.2 g of 1,17-diamino-3,6,9,12,15-pentaoxaheptadecane (25 mmol) in 75 ml of DMF under an argon atmosphere was treated with 3.41 g of N-succinimidyl biotin (10 mmol) added in portions over 1.0 hour. The resulting solution was stirred for four hours at ambient temperature. TLC (SiO$_2$, 70:10.1 CHCL$_3$—CH$_3$OH-conc. NH$_4$ OH) visualized by dimethylaminocinnamaldehyde spray reagent showed excellent conversion to a new product (Rf=0.18). The reaction mixture was divided in half and each half was absorbed onto SiO$_2$ and flash-chromatographed on 500 g of SIO$_2$-60 (230–400 mesh) using a 70:10.1 CHCl$_3$—CH$_3$OH-conc. NH$_4$OH solvent mixture. Fractions containing the product were polled and concentrated to a yield 2.42 g of a gelatinous, waxy solid. The product was precipitated as a solid from isopropanol-ether, washed with hexane, and dried at 55° C. (0.1 mm) to give 1.761 g of a white powder (35% yield).

Analysis: Calculated for $C_{22}H_{42}N_4O_7S \cdot 3/2\ H_2O$: C, 49.51; H, 8.50; N. 10.49. found: C, 49.59; H, 8.13; N, 10.39.

PMR: (90 MHz, dmso-$d_6$) δ: 1.1–1.7 (m, 6H); 2.05 (t, J=7Hz, 2H); 2.62 (t, J=4Hz, 1H); 2.74 (t, J=4Hz, 1H); 3.0–3.4 (m, 14H). 3.50 (s, 14H); 4.14 (m, 1H); 4.30 (m, 1H); 6.35 (d, J=4Hz, 1H); 7.80 (m, 1H).

CMR: (22.5 MHz, dmso-d6) δ: 25.2, 28.0, 28.2, 35.1, 40.6, 55.3, 59.2, 61.1, 69.6, 69.8, 71,2, 162.7, 172.1.

IR: (KBr) cm$^{-1}$: 2900, 2850, 1690, 1640, 1580, 1540, 1450, 1100.

Mass Spectrum (FAB) m/e: 507.3 (M+1, 56% )

Example 2: Preparation of 4'-Biotinyl-PEG-4,5'-dimethylangelicin

A solution of 203 mg of 1-amino-17-N-(biotinylamido)-3,6.9.12,15-pentaoxaheptadecane (0.4 mmol) in 1 ml of DMF under an argon atmosphere was treated with 78 of N,N-carbonyldimidazole (0.48 mmol). The resulting mixture was stirred for four hours and was then treated with 55 mg of 4'-aminomethyl-4,5'dimethylingelicin hydrochloride (0.2 mmol), 140 μl of diisopropylethylamine, and 100 μl of DMF. The resulting mixture was stirred overnight at 50° C. The mixture was then evaporated onto SiO$_2$ in vacuo and the resultant impregnated solid flash was chromatographed on 60 g of SiO$_2$ (230–400 mesh) eluted with 1.5 liters of 7% CH$_3$—CHCl$_3$ followed by 1 liter of 10% CH$_3$OH—CHCl$_3$. Fractions containing the product were pooled and concentrated to yield 72 mg of a glassy solid (47% yield).

PMR: (90 MHz, dmso-$d_6$) :δ 1.1–1.8 (m, 6H); 2.04 (bt, J=7Hz, 2H); 2.5 (s, 6H); 2.56 (m, 1H); 2.74 (bd, J=4Hz, 1H); 2.8–3.4 (m, 14H); 3.40 (m, 14H); 4.14 (m, 1H); 4.25 (m, 1H); 4.40 (bd, J=6Hz, 2H); 6.5 (m, 1H); 6.35 (s, 1H); 7.02 (s, 1H); 7.45 (d, J=8Hz, 1H); 7.62 (d, J=8Hz, 1H); 7.80 (m, 1H).

CMR: (22.5 MHz, dmso-$d_6$) δ: 11.9, 18.9, 25.3, 28.2 28.3, 33.4, 35.2, 55.4, 59.2, 61.0, 69.2, 69.6, 69.8, 70.0, 89.0, 107.8, 112.0, 113.1, 114.3, 120.6, 121.6, 153.6, 154.4, 155.6. 157.9, 159.5, 162.7, 172.1.

Literature Reference: F. Dall'Acqua, D. Vedaldi, S. Caffieri, A. Guiotto, P. Rodighiero, F. Baccichetti, F. Carlassare and F. Bordin, *J. Med. Chem.*, 24, 178 (1981).

Example 3: Colorimetric or Chemiluminescent Detection of the Nucleic Acid Hybrids

Example 3(a): Colorimetric Detection

Colorimetric detection of the biotinylated hybrids is carried out following the procedure and kit developed by Bethesda Research Laboratories (BRL), Gaithersburg, Md. 20877, U.S.A. The procedure is described in detail in a manual supplied with a kit by BRL, entitled "Products for Nucleic Acid Detection", "DNA Detection System Instruction Manual", Catalogue No. 8239SA.

Example 3(b): Chemiluminescent Detection

Chemiluminescent detection of the biotinylated hybrids is identical to the above method: the filters with the hybrids are saturated with BSA (bovine serum albumin) by immersing the paper in 3% BSA at 42° C. for 20 minutes. Excess BSA is removed by taking the paper out of the container, and blotting it between two pieces of filter paper. The paper is then incubated in a solution containing Streptavidin (0.25 mg/ml, 3.0 ml total volume), for 20 minutes at room temperature. It is then washed three times with a buffer containing 0.1M Tris-HCl, pH 7.5, 0.1M NaCl, 2 mM $MgCl_2$, 0.05% "TRITON X-100". Next the filter is incubated with biotinylated horseradish peroxidase (0.10 mg/ml) for 15 minutes at room temperature. This is followed by three washings with 0.1M Tris-HCl, pH 7.5, 0.1M NaCl, 2 mM $MgCl_2$ and 0.05% Triton X-100, and one washing with 10 mM Tris (pH 8.0) buffer. Chemiluminescent activation is conducted in two ways. (1) Spots are punched out and the discs containing the DNA are placed in a microtiter plate with wells that are painted black on the sides. After the punched paper circles are placed in the microtiter plate wells, 0.8 ml buffer containing 40 mM Tris and 40 mM ammonium acetate (pH 8.1) is added to each well. Then 10 μl of 1:1 mixture of 39 mM Luminol (in DMF) and 30 him $H_2O_2$ (in water) is added. Light emission is recorded on a "POLAROID" instant film by exposing it directly in the film holder. Alternatively (2), the paper is soaked in a solution containing 1:1 mixture of 0.5 mM Luminol and $H_2O_2$ and wrapped with a transparent "SARAN WRAP". The light emission is recorded on a "POLAROID" film as above.

Example 4: General Method of Labeling the Test Sample Nucleic Acids

High molecular weight DNA from a patient's sample is isolated by a method described in U.S. Pat. No. 4,395,486 (Wilson et al), the entire contents of which are incorporated by reference herein. The nucleic acid is dissolved in 10 mM borate buffer (pH 8.0) to a final concentration of approximately 20 μg/ml. To the nucleic acid solution "angelicin-peg-biotin" in aqueous solution is added to a final concentration of 10 μg/ml. The mixture is then irradiated at long wavelength irradiation for about 60 minutes using a black ray UVL 56 lamp. The product is ready for hybridization without purification. However, the product can be purified by dialysis or alcohol precipitation (U.S. Pat. No. 4,395,486) as is usually followed for nucleic acids.

Instead of nucleic acids, whole cell lysate can also be labeled following an identical procedure. The lysis is conducted by boiling the cells with 0.1N sodium hydroxide, followed by neutralization with hydrochloric acid.

When whole cells are used, the mixture of "PEG-ang-bio" and cells are incubated for at least 60 minutes prior to irradiation for efficient transport of the ligands. Many different variations of the above described methods can be adopted for labeling.

Example 5:

Alpha-thalassemia is associated with gene deletion. The detection of gene deletion by hybridization in a dot/slot blot format requires that the total amount of sample and its hybridizability are accurately known. Since the beta-globin gene is a single copy gene, simultaneous hybridization of a sample with beta-globin and alpha-globin and their relative amounts will indicate the amount of alpha-globin with the sample.

The format and hybridization conditions are the same as Rubin and Kan, supra, except probes, not test DNA, is immobilized. Hybridization conditions are also similar. The detection is done by using the BRL kit described supra following BRL's specifications.

The hybridization detection process are conducted in three steps as follows:

Step 1: Immobilization of the Probes

As described in Rubin and Kan, supra, 1.5 kb PstI fragment containing $alpha_2$ globin gene is used as a probe for alpha-thalassemia and for the beta-globin gene a 737 base pair probe produced by the digestion of pBR beta Pst (4.4 kb) is used. The beta-globin gene probe has been described in U.S. Pat. No. 4,395,486 (column 4). For the detection of gene deletion related to alpha-thalassemia, the amount of starting nucleic acid, hybridization efficiency and control samples are needed. The present invention avoids these problems by simultaneous hybridization with a single copy essential gene (e.g., beta-globin gene) when similar amounts of probes are immobilized side by side, labeled sample is hybridized, relative strength of signal intensity is a measure of relative amount of gene dosage present in the sample.

The probes (0.5, 1, 3 and 5 μg per 100 μl) are suspended in 10 mM tris HCl (pH 7) buffer, denatured with 20 μl 3M sodium hydroxide, at 100° C., for 5 minutes, an equivalent volume of 2M ammonium acetate, pH 5.0 is added to neutralize the solution, immediately after neutralization the probes for beta- and alpha-globin genes are applied in parallel rows to nitrocellulose filter paper under vacuum in a slot blot manifold, purchased from Scleicher and Schuell, (Keene, N.H., U.S.A.). The filter is then dried in vacuum at 80° C. for 60 minutes. It is then prehybridized for 4 hours in a mixture containing 50 mM sodium phosphate (pH 7) 45 mM sodium citrate, 450 mM sodium chloride, 50% (v/v) formamide, 0.2% each (w/v) of polyvinyl pyrrolidine, "FICOLL 400" and bovine serum albumin and 0.2 mg/ml alkali boiled salmon sperm DNA and 0.15 mg/ml yeast RNA.

Step 2: Labeling of the Test Sample

This was described above.

Step 3: Hybridization

The nitrocellulose strip containing the immobilized probes are hybridized with the labeled test sample in plastic bags (e.g., "SEAL-A-MEAL", "SEAL and SAVE", etc.). Hybridization solution is the same as prehybridization solution plus 10% dextran sulphate. Hybridization is done at 42° C. for 16 hours. After hybridization detection of biotin is conducted with a kit and procedure supplied by Bethesda Research Laboratory, Maryland, U.S.A., (catalogue No. 8239SA). Results of relative intensity of alpha- and beta- regions are used to estimate the extent of deletion of alpha-globin genes:

No signal on the alpha-globin side: all 4 alpha-globin genes missing.

Signal on the alpha-globin side is half as strong as on the corresponding beta-side: 3 alpha-globin genes missing.

Signals on alpha and beta side equivalent: 2 alpha-globin genes missing.

Signals on alpha side is stronger than the corresponding beta side (2 alpha=3 beta): 1 alpha-globin gene missing.

Example 6: Immobilization of an Oligonucleotide Sequence Specific for Hemoglobin Mutation It is known that an oligonucleotide cannot be easily immobilized onto nitrocellulose paper by a simple adsorption process. The present invention encompasses three different methods to incorporate an oligonucleotide sequence into a larger molecule capable of adsorption.

Method 1: Two oligonucleotides, one a 43met and the other a 16-mer, have been chemically synthesized in an automated synthesizer (Applied Biosystem 380B) by the phosphoramidite-method and phosphorylated at the 5' end by a T4-polynucleotide kinase mediated process according to Maniatis et al, *Molecular Cloning*, page 122. These oligonucleotides contain a segment of a 19 nucleotide long sequence specific for the detection of the mutation associated with sickle cell anemia.

43mer A & S (A=normal globin gene; S=sickle globin gene) were kinased according to Maniatis et al, *Molecular Cloning*, page 122, in two separate reactions, namely, one with $^{32}$P-ATP and one with no radioactive label. 0.4 μg $^{32}$P-43mer and 0.6 mg cold 43mer were mixed and purified on a spun column (G-25med in TE (Tris EDTA buffer)) to a final volume of 40 μl. Two dilutions were spotted on S & S (Schleicher & Schuell) nitrocellulose and nytran (nylon) membranes at 50 and 0.5 ng.

Method 2: The phosphorylated oligonucleotide products of method 1 were further elongated by making multimers of sequences by a ligase mediated process. The principle is described as follows:

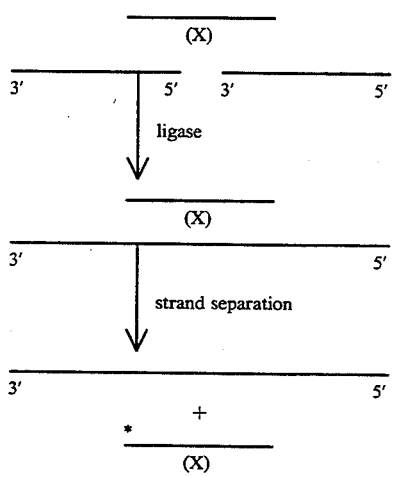

The product being of a higher molecular weight than an oligonucleotide it should be immobilizable by adsorption on to a nitrocellulose paper.

Aqueous solutions containing 4μg of $^{32}$P43mer and 3.7 μg 16ruer linker (X) were mixed and dried under vacuum. 6 mg of cold kinased 43mer was added and the sample was heated to 55° C. and cooled slowly to 0° C. to anneal. Ligation was carried out in 20 μl total reaction volume with 800 units of ligase (Pharmacia) at 15° C. for 4 hours. 1 mg (2 μl) was purified on a spun column (G-25med in TE) to a final volume of 40 μl. Two dilutions were spotted on nitrocellulose nylon membranes at 50 and 0.5 ng.

Method 3: The same as method 2, but ligation was not conducted. Instead of ligation, cross linking was conducted with an intercalator to keep the double stranded regions intact. Hence, the cross linked molecule will have several oligonucleotide sequences covalently linked to each other.

2 μg of $^{32}$P43mer (for sequence P-50) was added to 2.9 mg of a 16mer (for sequence P-50) linker and purified on a spun column (G25med in TE) to a final volume of 40 μl. 1. 6 mg of kinased 43mer was added and the samples were heated to 55° C. and cooled slowly to 0° C. to anneal. 25 μl of intercalation compound aminomethyltrioxsalen was added and the sample was irradiated for 30 minutes on ice in 500 μl total 10 mM borate buffer pH 8.2 with a long wave UV lamp model (UVL-21, =366 nM).

The probes modified by all three methods were then immobilized on to nitrocellulose and nylon paper and hybridized with labelled oligonucleotides. The results indicate that the sequence are immobilizable and hybridization fidelity remains intact.

Two dilutions of the products of methods 1 to 3 were spotted on nitrocellulose and nylon membranes at 50 and 0.5 ngs.

Whole filters were baked for 30 minutes in 80° C. vacuum oven and prehybridized in blotto (5% nonfat dry milk, 6XSSC, 20 mM Na-pyrophosphate) for 30 minutes in 50° C. oven.

Hybridization was carried out with primer extended 19'A & 19S' probes at 50° C. for one hour (3 strips/probe).

Filters were stringently washed for 15 minutes at room temperature in 6XSSC with slight agitation and 2×10 minutes at 57° C.

Air-dried filters were place on Whatman paper and autoradiographed at −70° C. overnight.

The results presented in FIG. 1 surprisingly indicate specific hybridization are obtained by immobilizing oligonucleotide probes.

Example 7: Hybridization with labeled genomic DNA for Non Radioactive Detection Human normal genomic (XX) DNA was photolabeled with "biotin-PEG-angelicin" (BPA) in 10 mM borate buffer pH 8.2 at a weight ratio of 0.3 to 1 (BPA:DNA) for 15 minutes on ice with a long wave UV lamp model UVL-21, =366 nm. No purification is necessary.

Target DNA oligonucleotides were directly immobilized on S & S nitrocellulose in 1 μl aliquots at the following concentration, and then baked in an 80° C. vacuum oven for 30 minutes. The amounts of the different immobilized probes are as follows:

| | | |
|---|---|---|
| 43-mer | (A) - Kinased (method 1) | 200 ng |
| 43-mer | (A) | 200 ng |
| 43-mer | (S) - Kinased (method 1) | 200 ng |
| 43-mer | (S) | 200 ng |
| M1319Ass | | 50 ng |
| M1319Sss | | 50 ng |
| M13737Ass | | 50 ng |
| BRL | Commercially biotinylated DNA | 200 pg |
| pUC19 | | 50 ng |

43-merA: 5' GGAT$_3$AAT$_4$CTCCTGAG-GAGAAGTCT GCT$_4$AATCTTAA 3'

*=T for 43-mer S 16-mer (Common to both A and S)
3'-TTKGAKTTCCTKAATT-5'

Filters were prehybridized in blotto (5% nonfat dry milk, 6XSSC, 20 mM Na-pyrophosphate) for 30 minutes in a 45° C. H$_2$O bath.

All 4 strips were hybridized in 2 mls solution containing 2 μg labeled XX DNA containing normal beta-globin gene (hybridization solution was blotto with 10% PEG) for 2 hours in 45° C. in a H$_2$O bath.

Figure 2:
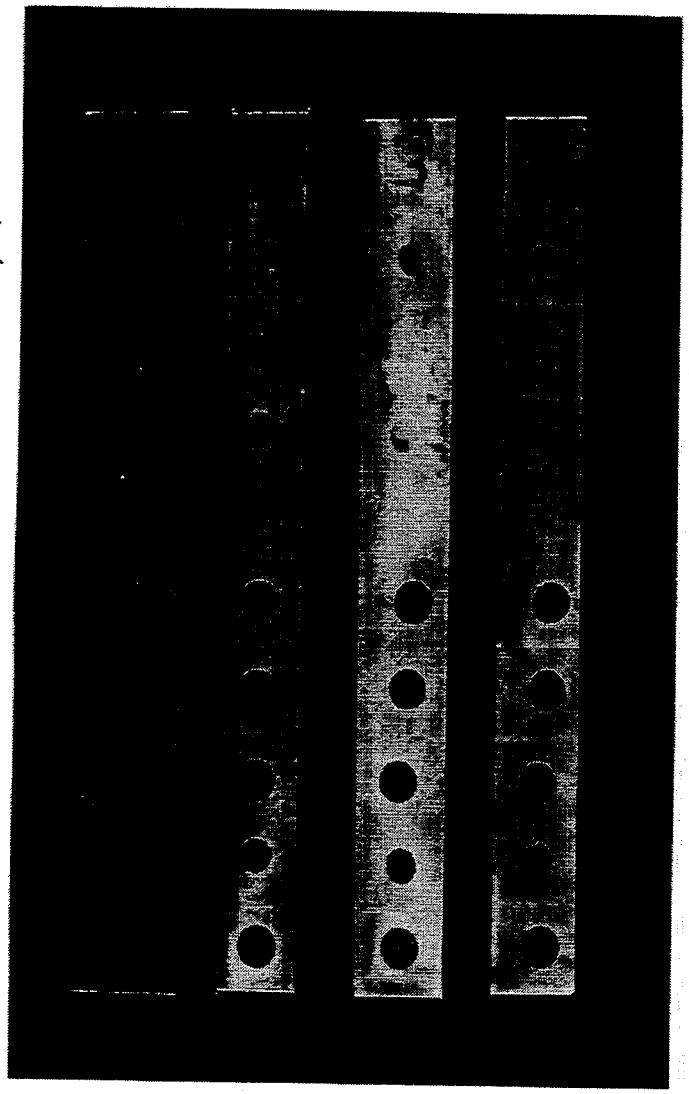
FIG. 2 is a photograph of results of hybridization with labeled genomic DNA for non radioactive detection.

A stringency wash was carried out as follows:
1×20′ at room temperature in 6XSSC
2×20′ at temperatures indicated in FIG. 2 with very little agitation.

50 ml centrifuge tubes were used for elevated temperature washes. Results are shown in FIG. 2.

Detection of biotin in the hybrid was carried out according to the Bethesda Research Laboratory, Bethesda, Md., U.S.A., manual using their kit for biotin detection. The results indicated specific hybridization.

Example 8: Immobilization of Whole Genomic DNA As Probes

Tens of milligram to gram amounts of DNA were prepared in the following manner from bacterial cells harvested from fermentor cultures. Bacteria were collected by centrifugation from 10 liter nutrient broth cultures grown in a New Brunswick Scientific Microferm Fermentor. Generally, cells in concentrated suspension were lysed by exposure to an ionic detergent such as SDS (Na dodecyl sulfate), then nucleic acids were purified from proteins and lipids by extraction with phenol and/or chloroform (J. Martour, *J. Mol. Biol.*, 3, 208–218, 1961). RNA was removed from the nucleic acids preparation by treatment of the DNA solution with 0.2 mg/ml ribonuclease at 37° C., then DNA was precipitated from solution by the addition of two volumes of ethanol. Bacterial DNA redissolved from the precipitate in a low salt buffer such as TE (10 mM Tris-HCl, pH 7.5, 1 mM Na$_2$ EDTA) was characterized with respect to purity concentration and molecular size, then approximately 1 microgram aliquots were denatured and immobilized as spots on nitrocellulose or nylon membranes for hybridization (Kafatos et al., *Nucleic Acids, Res.* 2, 1541–1552, (1979)). Denaturation was accomplished by exposure of the. DNA with approximately 0.1N NaOH. After denaturation the solution was neutralized, then the membrane was rinsed in NaCl/Tris-HCl, pH 7.5, and dried.

Example 9: Processing of a Test Sample for Cellular DNA Labeling

Samples of urine, for example (although the following can equally apply to suspensions of material form gonorrhea-suspect swabs, from meningitis-suspect cerebrospinal fluid, from contamination-suspect water samples, etc.), are centrifuged or filtered to wash and concentrate any bacteria in the sample. The bacteria are then lysed by exposure to either (i) 2 mg/ml lysozyme or lysostaphin then exposure to approximately 90° C. heat, (ii) 0.1 to 1.6N NaOH, or (iii) 1% Na dodecyl sulfate. After (ii) NaOH, the cell lysate solution is neutralized before labelling; after (iii) detergent lysis, DNA labelling is preceded by removal of the SDS with 0.5M K acetate on ice. Angelicin should be able to permeate intact cells so that DNA labeling can be accomplished before cell lysis. This in situ labeling simplifies the extraction procedure, as alkaline or detergent lysates can be incorporated directly into a hybridization solution.

Prior to hybridization, the labeled sample is denatured, and it should also preferably be reduced to short single stranded lengths to facilitate specific annealing with the appropriate unlabeled probe DNA. Methods of denaturation are known in the art. These methods include treatment with sodium hydroxide, organic solvent, heating, acid treatment and combinations thereof. Fragmentation can be accomplished in a controlled way be heating the DNA to approximately 80° C. in NaOH for a determined length of time, and this, of course, also denatures the DNA.

Example 10: Labeling of the Products of Example 9

(i) A test sample of about 10ml urine will contain $10^4$ or more infectious agents. After separation by centrifugation and washing, the pretreated cell lysate (step 2) was resuspended in 0.2 ml 10 mM sodium borate buffer (pH approximately 8). To this suspension, 10 μg of photolabelling reagent dissolved in ethanol (10 mg/ml), was added and mixed by shaking on a vortex mixer. The mixture was then irradiated at 365 nm for 30 minutes with a UVGL 25 device at its long wavelength setting. The UVGL device is sold by UVP Inc., 5100 Walnut Grove Avenue, P.O. Box 1501, San Gabriel, Calif. 91778, U.S.A.

(ii) The sample was also labeled with N-(4-azido-2-nitrophenyl)-N'-(N-d-biotinyl-3-aminopropyl)-N'-methyl-1,3-propanediamine (commercially available from BRESA, G.P.O. Box 498, Adelaide, South Australia 5001, Australia), following the procedure described by Forster et al (1985), supra for DNA.

(iii) When unlysed cells were used, the cell suspension in 0.2 ml 10 mM borate was incubated with the photoreagent for 1 hour prior to irradiation.

Example 11: Hybridization of the Products of Examples 8 and 10

Prior to hybridization, the membrane with spots of denatured unlabeled probe DNA was treated for up to 2 hours with a "prehybridization" solution to block sites in the membrane itself that could bind the hybridization probe. This and the hybridization solution, which also contained denatured labeled sample DNA, was comprised of approximately 0.9M Na$^+$, 0.1% SDS, 0.1–5% bovine serum albumin or nonfat dry milk, and optionally formamide. With 50% formamide, the prehybridization and hybridization steps were done at approximately 42° C.; without, the temperature was approximately 68° C. Prehybridized membranes can be stored for some time. DNA hybridization was allowed to occur for about 10 minutes or more, then unbound labeled DNA was washed from the membrane under conditions such as 0.018M Na$^+$ (0.1× SSC), 0.1% SDS, 68° C., that dissociate poorly base paired hybrids. After posthybridization washes, the membrane was rinsed in a low salt solution without detergent in anticipation of hybridization detection procedures.

Example 12: Detection of a Nucleic Acid Hybrid with Immunogold

Affinity isolated goat antibiotin antibody (purchased from Zymed Laboratories, San Francisco, Calif., U.S.A.) was adsorbed onto colloidal gold (20 nm) following the method described by its supplier (Janssen instruction booklet, Janssen Life Sciences Products, Piscataway, N.J. U.S.A.) and reacted with hybridized biotinylated DNA after blocking as in a colorimetric method. The signals were silver enhanced using a Janssen (B2340 BEERSE, Belgium) silver enhancement kit and protocol.

Example 13: Detection of Urinary Tract Infection in a Urine Sample

Urine samples were collected from a hospital where they were analyzed by microbiological methods and the results were kept secret until the hybridization diagnosis was conducted. Then they were compared ascertain the validity of the hybridization results.

1 ml of clinical sample (urine) suspected of UTI infections was centrifuged in a Brinkman micro centrifuge for 5 minutes. Then 0.1 ml of 1.2N sodium hydroxide was added and the suspension was heated to 100° C. to lyse the cells. The suspension was then diluted to 1 ml with 10 mM sodium borate buffer pH 8 and was neutralized with hydrochlorine acid to a pH of 7. To the solution, 50 μg "biotin-PEG-angelicin" (see Example 2) is added and the mixture was irradiated with a UVL 56 long wavelength UV lamp for 15 minutes. The irradiated sample (0.1 ml) was added to 3 ml 3XSSC of 5% nonfat dry milk 10% PEG with 0.2M sodium pyrophosphate and hybridization was conducted with probes (whole genomic DNA) immobilized onto nitrocellulose paper at 68° C. for 5 minutes to overnight. After hybridization detection was conducted according to Examples 3 or 12, the spots or the photographs were visually interpreted for the presence of specific bacteria in the test sample. A spot of human DNA was also present in the nitrocellulose paper for the detection of leucocytes. The presence of leucocytes was further verified with a common method using "LEUKOSTIX" (Miles Laboratories, Elkhart, Ind., U.S.A.).

Typical results (Tables 1 and 2) indicate that the hybridization diagnosis produces similar results in a shorter time then the corresponding microbiological assays. The present invention not only provides information related to species identification, but also the leucocyte content in a clinical sample.

TABLE 1

DIAGNOSIS OF CLINICAL URINE SAMPLES

| *HOSPITAL DIAGNOSIS | APPLICANTS' HYBRIDIZATION RESULTS | DETECTION SYSTEM |
|---|---|---|
| NEG | NEG | GOLD |
| NEG | NEG | GOLD |
| NEG | NEG | GOLD |
| NEG | E.c.-M | CHEMI |
| NEG | E.c.-VW | GOLD |
| NEG | E.c.-VW | GOLD |
| S+, C− | NEG | GOLD |
| S+, C− | E.c.-S | CHEMI |
| S+, C− | E.c.-S, Kl.-M | CHEMI |
| S+, C− | NEG | GOLD |
| S+, C− | NEG | GOLD |
| S+, C− | NEG | GOLD |
| S+, C− | E.c.-VW | GOLD |
| S+, C− | NEG | GOLD |
| S+, C− | E.c.-VW | GOLD |
| S+, C− | NEG | GOLD |
| S+, C− | NEG | GOLD |
| 100,000/mL E.c. | E.c.-S | GOLD |
| 100,000/mL E.c. | E.c.-S | CHEMI |
| 100,000/mL E.c. | E.c.-W | GOLD |
| 50,000/mL E.c. | E.c.-M | CHEMI |
| 50,000/mL E.c. | NEG | GOLD |
| E. coli | E.c.-S, Kl.-M | CHEMI |
| E. coli | E.c.-VS, Kl.-S | CHEMI |
| E. coli | E.c.-S, Kl.-S | CHEMI |
| E. coli/Klebsiella mix | E.c.-S, Kl.-W | GOLD |
| E. coli/Staph mix | E.c.-S, St.-M | CHEMI |
| Klebsiella spp. | E.c.-M, Kl.-W | CHEMI |
| 100,000/mL K. pneumoniae | E.c.-W, Kl-VW | GOLD |
| Enterobacter spp. | NEG** | GOLD |
| 100,000 Candida | NEG** | GOLD |
| 100,000/mL Proteus | Pr.-S, E.c.-W | GOLD |
| 10,000/mL Strep | NEG | CHEMI |
| Mixture of 3 unidentified Gm(+) | NEG | GOLD |

*diagnosis conducted by streaking urine on an agar plate and treating the plate under conditions so that the infectious organism can grow.
**Enterobacter/Candida probes not included in the hybridization assay, therefore, negative results are not surprising; given the high stringency conditions employed in the assay, cross-hybridization with species related to Enterobacter was not detected.

Abbreviations: VS=very strong; S=strong; M=medium; W=weak; and VW=very weak hybridization signals; GOLD=detection method according to Example 12; CHEMI=chemiluminescent detection according to Example 3 (b)

Applicants' hybridization results represent the result of a subjective interpretation of the intensity of the hybridization signals obtained after detection. DNAs from the organisms listed in column two are the only ones for which any hybridization signal was obtained. The panel of DNAs used for hybridization included E. coli ("E.c."), Klebsiella pneumoniae ("Kl"), Proteus vulgaris ("Pr"), Pseudomonas aeruginosa, Staphylococcus epidermatis ("SE"), Streptococcus faecalis and Homo sapiens.

TABLE 2

COMPARISON OF AMES LEUKOSTIX ASSAY WITH APPLICANT'S ASSAY

| "LEUKOSTIX" RESULT | APPLICANTS' HYBRIDIZATION RESULT | DETECTION SYSTEM |
|---|---|---|
| 3+ | VS | GOLD |
| 3+ | S | CHEMI |
| 3+ | S | CHEMI |
| 3+ | M | CHEMI |
| 3+ | M | CHEMI |
| 3+ | S | GOLD |
| 3+ | S | GOLD |
| 3+ | VS | GOLD |
| 3+ | VS | GOLD |
| 3+ | VS | GOLD |
| 3+ | VS | GOLD |
| 2+ | S | CHEMI |
| 2+ | S | CHEMI |
| 2+ | S | CHEMI |
| 2+ | S | CHEMI |
| 2+ | S | GOLD |
| 2+ | S | GOLD |
| 2+ | S | GOLD |
| 2+ | S | GOLD |
| 2+ | S | GOLD |
| 1+ | S | GOLD |
| 1+ | VS | GOLD |
| 1+ | VW | GOLD |
| TRACE/1+ | M | CHEMI |
| TRACE | VS | CHEMI |
| TRACE | W | GOLD |
| TRACE | W | GOLD |
| TRACE | VS | GOLD |
| NEG | S | CHEMI |
| NEG | S | CHEMI |
| NEG | M | CHEMI |
| NEG | VW | GOLD |
| NEG | VW | GOLD |
| NEG | NEG | GOLD |
| NEG | NEG | GOLD |
| NEG | W | GOLD |
| NEG | W | GOLD |

TABLE 2-continued
COMPARISON OF AMES LEUKOSTIX ASSAY WITH APPLICANT'S ASSAY

| "LEUKOSTIX" RESULT | APPLICANTS' HYBRIDIZATION RESULT | DETECTION SYSTEM |
|---|---|---|
| NEG | W | GOLD |

The hybridization results summarized in column 2 of Table 2 represent subjective interpretations of the intensity of hybridization signal obtained when labeled urine samples described in Table 1 were hybridized with genomic human DNA.

The "LEUKOSTIX" assay is a colorimetric reagent strip assay. Color development on the reagent strip is compared to a chart provided with the assay reagent strips and ranges from negative (no color development) to 3+ (very strong color development).

Example 14: Lysis of Cells

A 1.0 mL aliquot of cell suspension was centrifuged and the cell pellet resuspended in 100μL of unbuffered NaOH solution. The sample was then exposed to high temperature for a short time and then diluted to the original volume using 10 mM borate buffer. The pH of the solution was then adjusted to neutral with HCl.

Table 4 shows the efficiency of lysis of two different Gram positive cocci, *Staphylococcus epidermidis* and *Streptococcus faecalis*, at varying NaOH concentrations at either 68° C. or 100° C. In this Example, the absorbance of the 10 mL aliquots at 600 nm was recorded before centrifugation. After centrifugation, the cell pellets were resuspended in varying concentrations of NaOH (100 μL) and duplicate samples of each exposed to 68° C. for 10 minutes or 100° C. for 5 minutes. Each sample was then diluted to 1.0 mL and the absorbance at 600 nm again recorded. Since the beginning and ending volumes are identical, the beginning and ending absorbance at 600 nm provides a direct measurement of lysis efficiency.

Whereas Gram negative organisms lysed efficiently in as low as 0.1N NaOH, Table 4 shows clearly that efficient lysis is a function of both NaOH concentration and temperature, such that higher NaOH concentrations are required as the incubation temperature decreases. At 100° C. (maximum temperature at 1 atmosphere) a concentration of at least 1.6N NaOH was required for efficient lysis of *S. epidermidis* and *S faecalis*. If lower temperatures are desirable or necessary, then higher concentrations of NaOH will be required to maintain lysis efficiency.

TABLE 3
EFFICIENCY OF LYSIS OF GRAM POSITIVE BACTERIA AT VARIOUS CONCENTRATIONS OF NaOH AT 68° C. and 100° C.

| | 100° C./5 Minutes | | | 68° C./10 Minutes | | |
|---|---|---|---|---|---|---|
| [NaOH] | OD600 PRE | OD600 POST | % LYSIS | OD600 PRE | OD600 POST | % LYSIS |
| *Streptococcus faecalis* | | | | | | |
| 0N | 0.475 | 0.366 | 23 | 0.512 | 0.357 | 30 |
| 0.1 | .509 | .261 | 50 | .513 | .238 | 54 |
| 0.2 | .512 | .194 | 62 | .514 | .259 | 50 |
| 0.4 | .504 | .175 | 65 | .513 | .150 | 71 |
| 0.8 | .506 | .113 | 78 | .505 | .147 | 71 |
| 1.2 | .498 | .082 | 84 | .498 | .150 | 70 |
| 1.6 | .487 | .061 | 88 | .426 | .099 | 77 |
| *Staphylucuccus epidermidis* | | | | | | |
| 0N | 0.667 | 0.558 | 16 | 0.690 | 0.560 | 19 |
| 0.1 | .681 | .396 | 42 | .701 | .441 | 37 |
| 0.2 | .674 | .296 | 60 | .699 | .414 | 41 |
| 0.4 | .699 | .183 | 74 | .730 | .309 | 58 |
| 0.8 | .705 | .091 | 87 | .715 | .187 | 74 |
| 1.2 | .680 | .070 | 90 | .719 | .090 | 88 |
| 1.6 | .693 | .035 | 95 | .660 | .040 | 94 |

Example 15: Direct Labeling of Nucleic Acids in an Infected Urine Sample

A set of clinical urine test samples was collected from a hospital. 1 ml of urine was deposited in a polypropylene tube (1.5 ml). To the urine 150 1 of 8 N-sodium hydroxide solution in water was added. The mixture was maintained in a boiling water bath for five minutes. The alkaline suspension was then transferred to another tube containing 0.3 g of solid boric acid for neutralization. The mixture was shaken well by hand for mixing and solubilization. To this mixture, 10 microgram of the photolabeling reagent "bio-PEG-Ang", as used in Example 10 (i) was added (10 microliter of 1 mg/ml in water). The mixture was then irradiated for 60 minutes using a hand held UV lamp (UVL25) at a long wavelength setting. The tube was kept on ice during irradiation.

A nitrocellulose paper strip containing immobilized unlabeled genomic DNA probes (as used in Example 8), 700 microliter mixture containing 5% non-fat dry milk, 10% polyethylene glycol (MW-6000), 10mM sodium pyrophosphate, all in 3 x SSC and 300 μl labeled test samples were placed in a seal-a-meal bag. The bag was heat sealed. Hybridization was then conducted for two hours at 68° C. by incubating the sealed bag in a water bath.

After hybridization, the nitrocellulose strip was washed at 68° C. with 0.1× SSC, 0.1% SDS for 30 minutes. The unsaturated sites were then blocked by immersing the paper in 3% BSA solution in 0.1 mM tris, 0.1M sodium chloride, 2 mM magnesium chloride for 30 minutes. The hybrid was then detected by either immunogold, or by chemiluminescence or by the BRL method (see Examples 2, 3(a) or 3(b)). For every sample, the diagnosis was also done by bacteriological growth methods. The results were then compared for validity of the present method.

It will be appreciated that the instant specification and claims are set forth by way of illustration and not limitation, and that various modifications and changes may be made without departing from the spirit and scope of the present invention.

What is claimed is:

1. A method for detecting at least one polynucleotide sequence from a microorganism or eucaryotic source in a biological test sample, comprising the steps of:
   (a) without prior centrifugation or filtration treating said biological test sample to lyse cells and to release nucleic acids therefrom,
   (b) without purification or isolation of specific nucleic acid sequences, photochemically labeling released sample nucleic acids directly in the lysate produced in step (a), (c) contacting the resulting labeled nucleic acids, under hybridization conditions, with at least one immobilized oligonucleotide or nucleic acid probe hybridizable with the sequence or sequence to be detected, thereby to form hybridized labeled nucleic acids, and (d) assaying for the hybridized nucleic acids by detecting the label.

2. The method according to claim 1, wherein the biological test sample is selected from the group consisting of urine, blood, cerebrospinal fluid, pus, amniotic fluid, tears, sputum, saliva, lung aspirate, vaginal discharge, stool, a solid tissue sample, a skin swab sample, a throat swab sample and a genital swab sample.

3. The method according to claim 1, wherein said labeling is effected by photochemically reacting a labeled form of a nucleic acid binding ligand with the sample nucleic acids.

4. The method according to claim 1, wherein the nucleic acids released from the sample are in double-standard form and, prior to step (c), the labeled nucleic acids are denatured to provide labeled single-stranded nucleic acids.

5. The method according to claim 1, wherein the biological sample is a eucaryotic source selected from the group consisting of algae, protozoa, fungi, slime molds and mammalian cells.

6. The method according to claim 1, wherein the biological sample is a microorganism selected from the group consisting of Escherichia, Proteus, Klebsiella, Staphylococcus, Streptococcus, Pseudomonas and Lactobacillus.

7. The method according to claim 1, wherein lysis in (a) is effected by treatment with alkali.

8. The method according to claim 1, wherein the label in (b) is selected from the group consisting of a protein binding ligand, haptens, antigen, fluorescent compound, dye, radioactive isotope and enzyme.

9. The method according to claim 1, wherein in (c) the probe is immobilized by covalent coupling or adsorption to a solid surface.

10. The method according to claim 9, wherein the probe is immobilized in the form of at least one dot on a solid support strip.

11. The method according to claim 1, wherein in (c) the hybridization is accelerated by the addition of polyethylene glycol.

* * * * *

UNITED STATES PATENT AND TRADEMARK OFFICE
CERTIFICATE OF CORRECTION

PATENT NO : 5,348,855
DATED : September 20, 1994
INVENTOR(S): Nanibhushan DATTAGUPTA, ET AL.

It is certified that error appears in the above-identified patent and that said Letters Patent is hereby corrected as shown below:

Item [63],

Title Page "Related U.S. Application Data", line 3, cancel "December 19, 1986" and substitute --December 29, 1986--

Signed and Sealed this

Eighth Day of February, 2000

*Attest:*

Q. TODD DICKINSON

*Attesting Officer*     *Commissioner of Patents and Trademarks*